(12) United States Patent
Smith et al.

(10) Patent No.: US 7,277,756 B2
(45) Date of Patent: Oct. 2, 2007

(54) RISK OF DEATH INDICATOR

(75) Inventors: Mitchell Smith, Mahtomedi, MN (US); Mark Schwartz, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 370 days.

(21) Appl. No.: 10/919,075

(22) Filed: Aug. 16, 2004

(65) Prior Publication Data
US 2006/0036292 A1 Feb. 16, 2006

(51) Int. Cl.
*A61B 5/0468* (2006.01)
*A61N 1/365* (2006.01)

(52) U.S. Cl. .......... 607/18; 600/515; 607/14; 607/19; 607/20

(58) Field of Classification Search ............ None
See application file for complete search history.

(56) References Cited

U.S. PATENT DOCUMENTS

| 5,273,049 | A | 12/1993 | Steinhaus et al. ............ 128/696 |
| 5,782,881 | A * | 7/1998 | Lu et al. ......................... 607/9 |
| 6,076,015 | A | 6/2000 | Hartley et al. ................ 607/20 |
| 6,266,554 | B1 | 7/2001 | Hsu et al. ..................... 600/515 |
| 6,272,377 | B1 | 8/2001 | Sweeney et al. ............. 600/515 |
| 6,308,095 | B1 | 10/2001 | Hsu et al. ..................... 600/518 |
| 6,449,503 | B1 | 9/2002 | Hsu ............................. 600/518 |
| 6,490,485 | B1 | 12/2002 | Sun et al. ..................... 607/20 |
| 6,718,197 | B1 * | 4/2004 | Carlson et al. ............. 600/515 |
| 2003/0055461 | A1 | 3/2003 | Girouard et al. ............. 607/17 |
| 2004/0093035 | A1 | 5/2004 | Schwartz et al. .............. 607/5 |
| 2005/0065443 | A1 * | 3/2005 | Ternes ........................ 600/509 |

OTHER PUBLICATIONS

Frolkis, Joseph P., et al., "Frequent Ventricular Ectopy after Exercise as a Predictor of Death", *The New England Journal of Medicine*, vol. 348, No. 9, (including 1 page correction, published in vol. 348, No. 15, at p. 1508,(Feb. 27, 2003),781-790.

* cited by examiner

*Primary Examiner*—Kristen Droesh Mullen
(74) *Attorney, Agent, or Firm*—Schwegman, Lundberg & Woessner, P.A.

(57) ABSTRACT

A system comprising an implantable medical device (IMD). The IMD comprises a ventricular heart signal sensing circuit to provide a ventricular heart signal, at least one sensor operable to provide an electrical signal representative of patient activity, a sensor interface circuit coupled to the at least one sensor to provide an activity signal, and a controller circuit coupled to the heart signal sensing circuit and the sensor interface circuit. The controller circuit is operable to determine whether ventricular ectopy occurs during recovery from exercise using the heart signal, and to set at least one warning indicator if ventricular ectopy occurs during the recovery from exercise.

31 Claims, 6 Drawing Sheets

RISK OF DEATH INDICATOR

TECHNICAL FIELD

The field generally relates to implantable medical devices and, in particular, but not by way of limitation, to a system and method for providing an indicator of increased risk of death.

BACKGROUND

During a normal contraction, the right ventricle of a heart pumps deoxygenated blood to the lungs and the left ventricle pumps oxygen-enriched blood and nutrients to the organs and blood vessels of the body. Inefficient pumping by the ventricular chambers may result in an inefficient amount of blood pumped to the body and an insufficient amount of fluid being pumped away from the lungs. If the cells of a heart do not receive enough oxygen and nutrients a heart attack can occur.

Certain abnormal ventricular contractions in a patient are sometimes referred to as ventricular ectopy. Exercise-induced ventricular ectopy predicts an increased risk of death for an individual. Dr. Joseph Froklis of the Cleveland Clinic Foundation conducted a study that concluded that post-exercise ventricular ectopy is a better predictor of an increased risk of death than exercise-induced ventricular ectopy. (See Dr. Joseph Froklis et al., "Frequent Ventricular Ectopy after Exercise as a Predictor of Death," 348 NEJM 781, 781 (2003)). The study defined ventricular ectopy as the presence of seven or more premature beats per minute, ventricular bigeminy or trigeminy, ventricular couplets or triplets, ventricular tachycardia, ventricular flutter, torsade de pointes, or ventricular fibrillation. Post-exercise refers to a period of recovery from exercise when reactivation of parasympathetic heart activity occurs.

SUMMARY

Systems and methods are provided for detecting ventricular ectopy in relation to exercise. A system embodiment comprises an implantable medical device (IMD). The IMD comprises a ventricular heart signal sensing circuit to provide a ventricular heart signal, at least one sensor operable to provide an electrical signal representative of patient activity, a sensor interface circuit coupled to the at least one sensor to provide an activity signal, and a controller circuit coupled to the heart signal sensing circuit and the sensor interface circuit. The controller circuit is operable to determine whether ventricular ectopy occurs during recovery from exercise using the heart signal, and to set at least one warning indicator if ventricular ectopy occurs during the recovery from exercise.

A method embodiment comprises monitoring a heart signal including ventricular depolarizations of a patient using an implantable medical device, monitoring an activity level of the patient to detect exercise and recovery from exercise, determining whether ventricular ectopy occurs during the recovery from exercise using the heart signal, and providing at least one warning if at least one instance of ventricular ectopy occurs during the recovery from exercise.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The present application discusses, among other things, systems and methods for detecting ventricular ectopy in relation to exercise. Implantable medical devices (IMDs) are devices designed to be implanted into a patient. Some examples of these devices include cardiac rhythm management devices such as implantable pacemakers and implantable cardioverter defibrillators (ICDs). The devices are used to treat patients using electrical therapy and to aid a physician or caregiver in patient diagnosis through internal monitoring of a patient's condition. The devices may include electrical leads in communication with sense amplifiers to monitor electrical heart activity within a patient, and often include sensors to monitor other internal patient parameters. Some IMDs are able to detect when a patient is exercising. Additionally, some IMDs are able to communicate with external devices by wireless communication signals.

By detecting ventricular ectopy from the electrical activity and determining whether the ventricular ectopy occurs during exercise, during a period of recovery from exercise, or both, the IMD can provide a warning of an increased risk of death of a patient. In one embodiment, the warning can be an alarm from the device itself, such as an audio alarm. In another embodiment, the IMD transmits the warning to an external device which provides the warning to either a caregiver or a patient.

Figure 1:
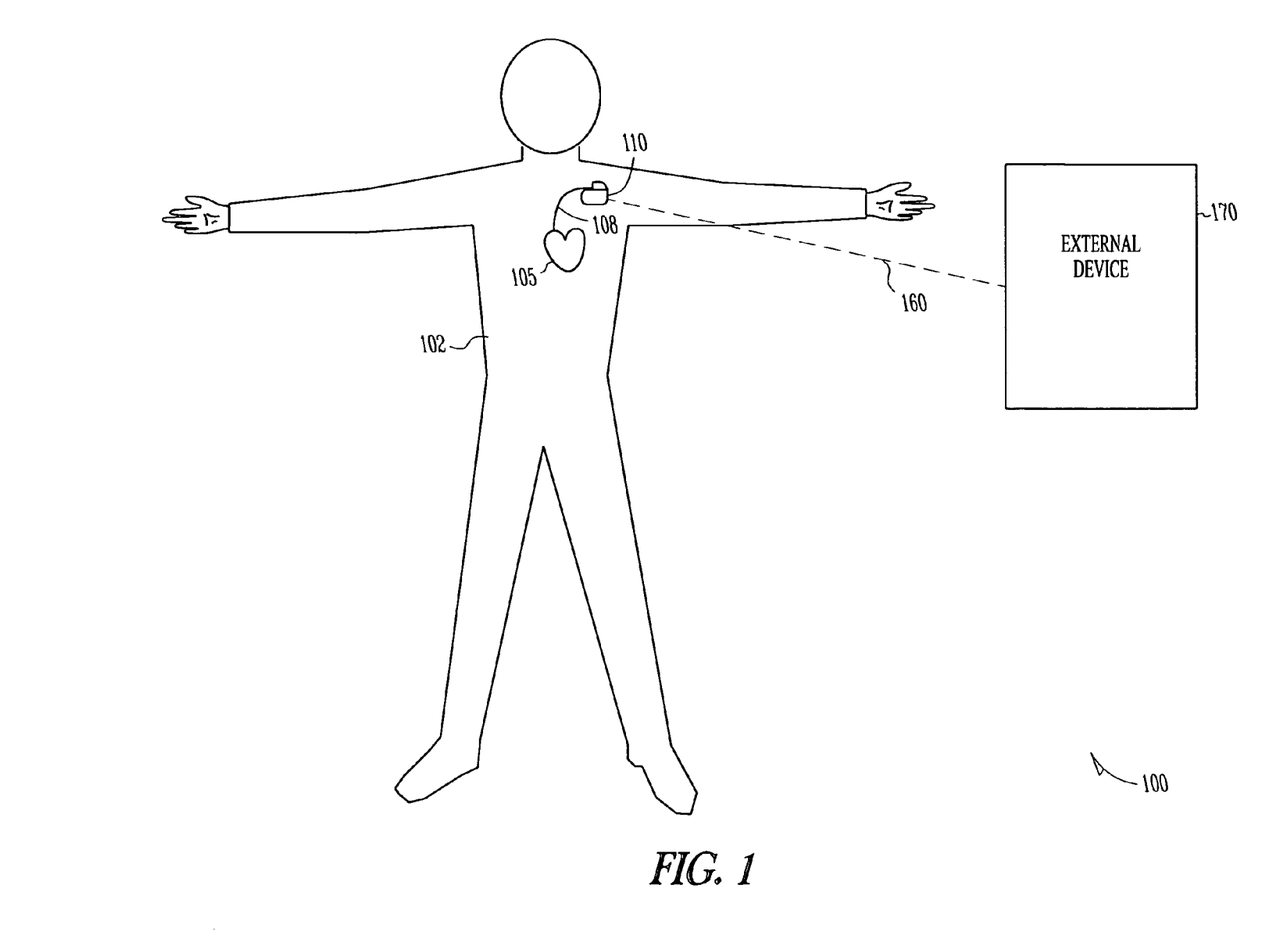
FIG. 1 illustrates an embodiment of a system that uses an implantable medical device.

FIG. 1 illustrates an embodiment of a system 100 that uses an implantable medical device (IMD) 110. The system 100 shown is one embodiment of portions of a system 100 used to treat a cardiac arrhythmia. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also includes an IMD programmer or other external system 170 that typically provides wireless communication signals 160 to communicate with the IMD 110, such as by using telemetry or radio frequency (RF) signals.

Cardiac lead 108 includes a proximal end that is coupled to IMD 110 and a distal end, coupled by an electrode or electrodes to one or more portions of a heart 105. The electrodes are for delivering atrial and/or ventricular cardioversion/defibrillation and/or pacing and/or resynchronization therapy to the heart 105. IMD 110 includes components that are enclosed in a hermetically-sealed canister or "can." Additional electrodes may be located on the can, or on an insulating header, or on other portions of IMD 110, for providing unipolar pacing and/or defibrillation energy in conjunction with the electrodes disposed on or around heart 105. The lead 108 or leads and electrodes are also used for sensing electrical activity of a heart 105.

Figure 2:
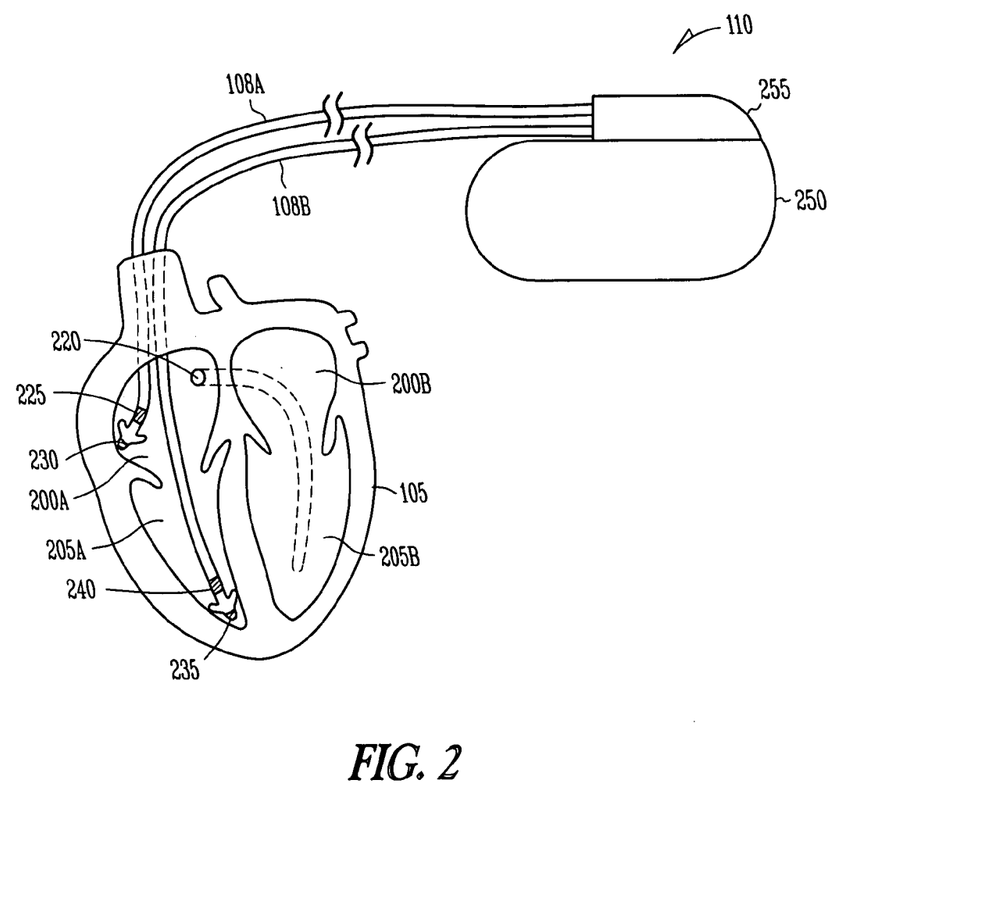
FIG. 2 illustrates an embodiment of an implantable medical device coupled by one or more leads to a heart.

FIG. 2 illustrates an IMD 110 coupled by one or more leads 108A-B to heart 105. Heart 105 includes a right atrium 200A, a left atrium 200B, a right ventricle 205A, a left ventricle 205B, and a coronary sinus 220 extending from right atrium 200A. In this embodiment, atrial lead 108A includes electrodes (electrical contacts, such as ring electrode 225 and tip electrode 230) disposed in, around, or near an atrium 200 of heart 105 for sensing signals and/or delivering pacing therapy to the atrium 200. Lead 108A optionally also includes additional electrodes, such as for delivering atrial and/or ventricular cardioversion/defibrillation and/or pacing or resynchronization therapy to heart 105.

Ventricular lead 108B includes one or more electrodes, such as tip electrode 235 and ring electrode 240, for delivering sensing signals and/or delivering pacing therapy. Lead 108B optionally also includes additional electrodes, such as for delivering atrial and/or ventricular cardioversion/defibrillation and/or pacing therapy to heart 105. IMD 110 includes components that are enclosed in a hermetically-sealed canister or "can" 250. Additional electrodes may be located on the can 250, or on an insulating header 255, or on other portions of IMD 110, for providing unipolar pacing and/or defibrillation energy in conjunction with the electrodes disposed on or around heart 105. Other forms of electrodes include meshes and patches which may be applied to portions of heart 105 or which may be implanted in other areas of the body to help "steer" electrical currents produced by IMD 110. In one embodiment, one of atrial lead 108A or ventricular lead 108B is omitted, i.e., a "single chamber" device is provided, rather than the dual chamber device illustrated in FIG. 2. In another embodiment, additional leads are provided for coupling the IMD 108 to other heart chambers and/or other locations in the same heart chamber as one or more of leads 108A-B. The present methods and systems will work in a variety of configurations and with a variety of electrical contacts or "electrodes."

Figure 3:
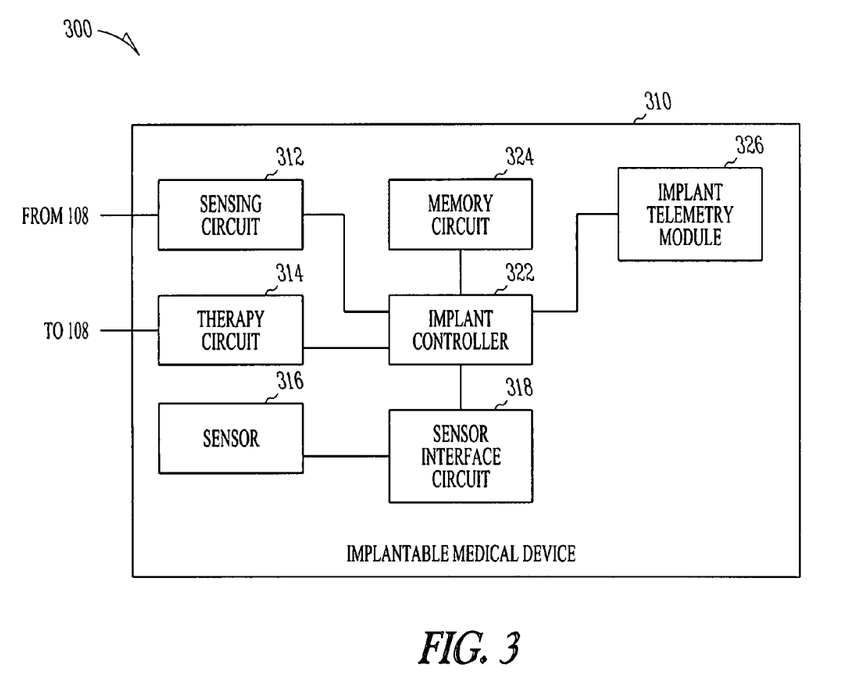
FIG. 3 is an illustration of portions of an embodiment of an implantable medical device used to detect ventricular ectopy in relation to exercise.

FIG. 3 is an illustration 300 of portions of an IMD 310 used to detect ventricular ectopy in relation to exercise. The IMD 310 comprises a ventricular heart signal sensing circuit 312 to provide a ventricular heart signal, at least one sensor 316 operable to provide an electrical signal representative of patient exercise activity level, a sensor interface circuit 318 to provide a responsive activity signal, and a controller circuit 322.

In one embodiment, the controller circuit 322 is operable to determine whether ventricular ectopy occurs during recovery from exercise using the heart signal, such as by executing an algorithm or algorithms implemented by hardware, software, firmware or any combination of hardware, software or firmware. The controller circuit 322 is operable to set at least one warning indicator if ventricular ectopy occurs during the recovery from exercise. In another embodiment, the controller circuit 322 is operable to determine whether ventricular ectopy occurs during exercise using the heart signal and to set at least one warning indicator if ventricular ectopy occurs during the exercise. In yet another embodiment, the controller is operable to determine whether ventricular ectopy occurs during both exercise and recovery from exercise and to set at least one warning indicator if ventricular ectopy occurs during exercise and during recovery from exercise.

Figure 4:
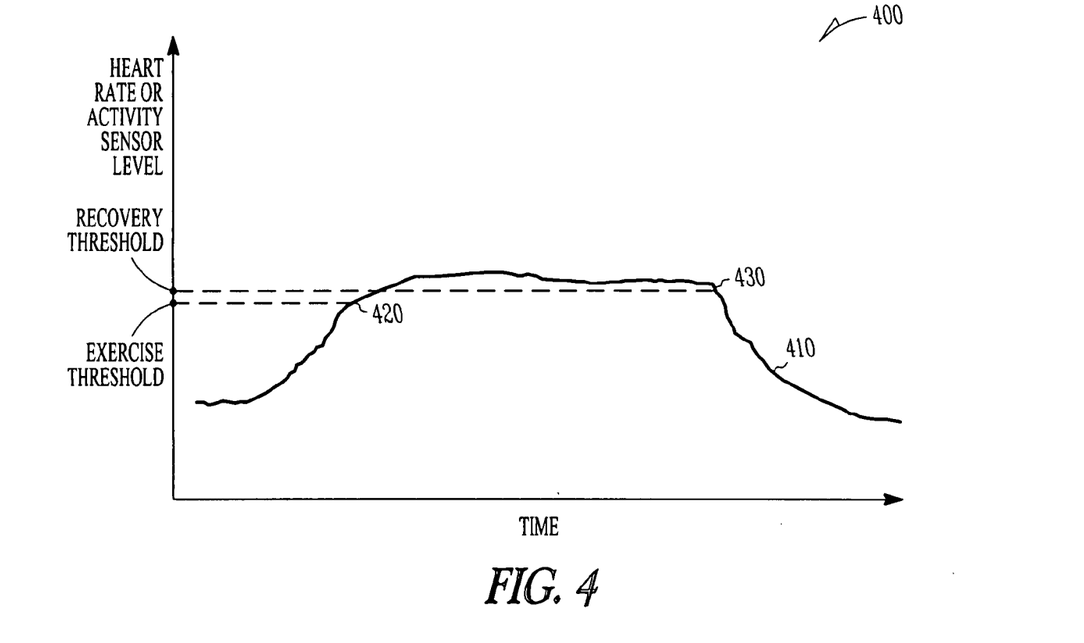
FIG. 4 shows a graph of heart rate or activity sensor level versus time.

FIG. 4 shows a graph 400 of heart rate or activity sensor level versus time. In one embodiment, the controller circuit 322 extracts heart rate information 410 from the heart signal to detect that a patient is exercising and/or recovering from exercise. In one embodiment, the controller circuit 322 detects that a patient is exercising when a rate exceeds an exercise threshold value 420. The controller circuit 322 detects recovery from exercise when the heart rate drops below a recovery threshold value 430. In another embodiment, the exercise threshold value 420 and the recovery threshold value 430 are the same.

Returning to FIG. 3, in other embodiments of the IMD 310, the controller circuit 322 is operable to detect exercise and/or recovery from exercise using the activity signal provided by the sensor 316 and the sensor interface circuit 318. In one such embodiment, the sensor 316 includes an accelerometer. In another embodiment, the sensor 316 includes a minute ventilation (MV) sensor or sensors. An example of determining MV can be found in U.S. Pat. No. 6,076,015, "Rate Adaptive Cardiac Rhythm Management Device Using Transthoracic Impedance," Hartley et al, which is incorporated herein by reference. In yet another embodiment, the sensor 316 includes both an MV sensor and an accelerometer sensor. The outputs of the sensors are then blended to combine the indications of activity.

As stated previously, the controller circuit 322 is operable to determine whether ventricular ectopy occurs using the heart signal. In some embodiments, the physician or caregiver can define what kind of ventricular ectopy is to be detected by the IMD. For example, a caregiver can define ventricular ectopy to include one or a combination of a presence of seven or more premature beats per minute, ventricular bigeminy or trigeminy, ventricular couplets or triplets, ventricular tachycardia, ventricular flutter, torsade de pointes, and ventricular fibrillation. One of skill in the art would understand, upon reading this detailed description, that other definitions of ventricular ectopy are within the scope of the present application.

In one embodiment of an IMD 310 that detects ventricular ectopy, the IMD 310 includes a memory 324. In the embodiment, the memory stores at least one morphology template representative of ventricular ectopy. The embodiment also includes a sampling circuit coupled to the sensing circuit and the controller circuit to provide sampled values of the ventricular heart signal. The controller circuit 322 is further operable to determine whether ventricular ectopy occurs using a comparison of the sampled values to the at least one morphology template representative of ventricular ectopy. A discussion of classifying heart signals using comparisons to morphology templates can be found in U.S. Pat. No. 6,266,554, "System and Method for Classifying Cardiac Complexes," Hsu et al, which is incorporated herein by reference. In Hsu, the morphology of a cardiac complex is compared to the morphology of a template cardiac complex representing a predetermined cardiac condition. Based on this comparison, the cardiac complex is classified as either belonging or not belonging to the predetermined cardiac condition.

Thus, a certain kind or a combination of ventricular ectopies can be detected by comparing a sensed cardiac complex to a template representing the desired ventricular ectopy.

Other embodiments of an IMD 310 include a telemetry module 326 to communicate with an external device or system using wireless communications. In such embodiments of a system that includes an IMD 310 and an external device, the external device includes a display operable to display information related to ventricular ectopy occurring during at least one of exercise and recovery from exercise. In one embodiment, the information related to ventricular ectopy includes a warning indicator that indicates whether ventricular ectopy occurred during at least one of exercise and recovery from exercise. In one example, the warning is indicated when the implantable medical device is interrogated by the external device. In another embodiment, the external device is operable by a patient, and the warning indicator includes an alarm.

Figure 5:
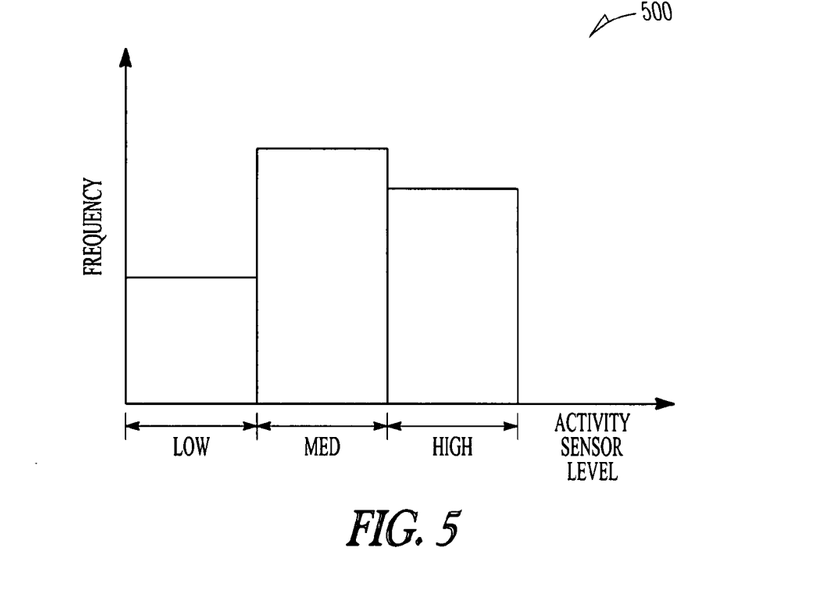
FIG. 5 shows an example of a histogram of ventricular ectopy during at least one of exercise and recovery from exercise.

In another embodiment, the memory 324 stores information related to ventricular ectopy events that occur during at least one of exercise and recovery from exercise. The information can be transmitted to the external device. In another embodiment, the information related to ventricular ectopy includes a histogram of ventricular ectopy during at least one of exercise and recovery from exercise. FIG. 5 shows an example of such a histogram 500. In the example, the histogram shows a relation of frequency of ventricular ectopy to activity sensor output level. The ventricular ectopy episodes may be during exercise and/or during recovery from exercise. The horizontal axis of the histogram is broken up into three ranges of sensor output operation. The histogram shows the relative frequency of ectopy with sensor output level. In another example, the horizontal axis of the histogram includes three "bins," where the bins include "during exercise," "during recovery from exercise" and "other." The histogram would show the relative frequency of ventricular ectopic episodes in relation to exercise.

In yet another embodiment, the information related to ventricular ectopy includes trending of ventricular ectopy during at least one of exercise and recovery from exercise. For example, trending of the information may show that the frequency of ventricular ectopy during exercise is increasing over time. Or, it may show that a duration of ventricular ectopy during recovery from exercise is increasing over time. In yet another embodiment, the external device is operable to communicate with a communication network, such as a hospital computer network, the internet, or a wireless communication network.

Returning to FIG. 3, other embodiments of an IMD 310 include a therapy circuit coupled to the controller circuit 322. In such an embodiment, the therapy circuit includes the pacing circuit 314 in FIG. 3. The controller circuit 322 is further operable to modify an output of the therapy circuit if ventricular ectopy occurs during at least one of exercise and recovery from exercise. For example, if the ventricular ectopy includes tachyarrhythmia, the controller circuit may initiate anti-tachyarrhythmia pacing using the pacing circuit 314. In another embodiment, the IMD 310 includes an implantable cardioverter/defibrillator and the IMD 310 initiates defibrillation shock therapy if the ventricular ectopy includes tachyarrhythmia. In yet another embodiment, the IMD 310 provides drug therapy and if the ventricular ectopy is of a type treatable with drugs, the therapy circuit initiates delivery of the drug therapy when the ventricular ectopy occurs.

Figure 6:
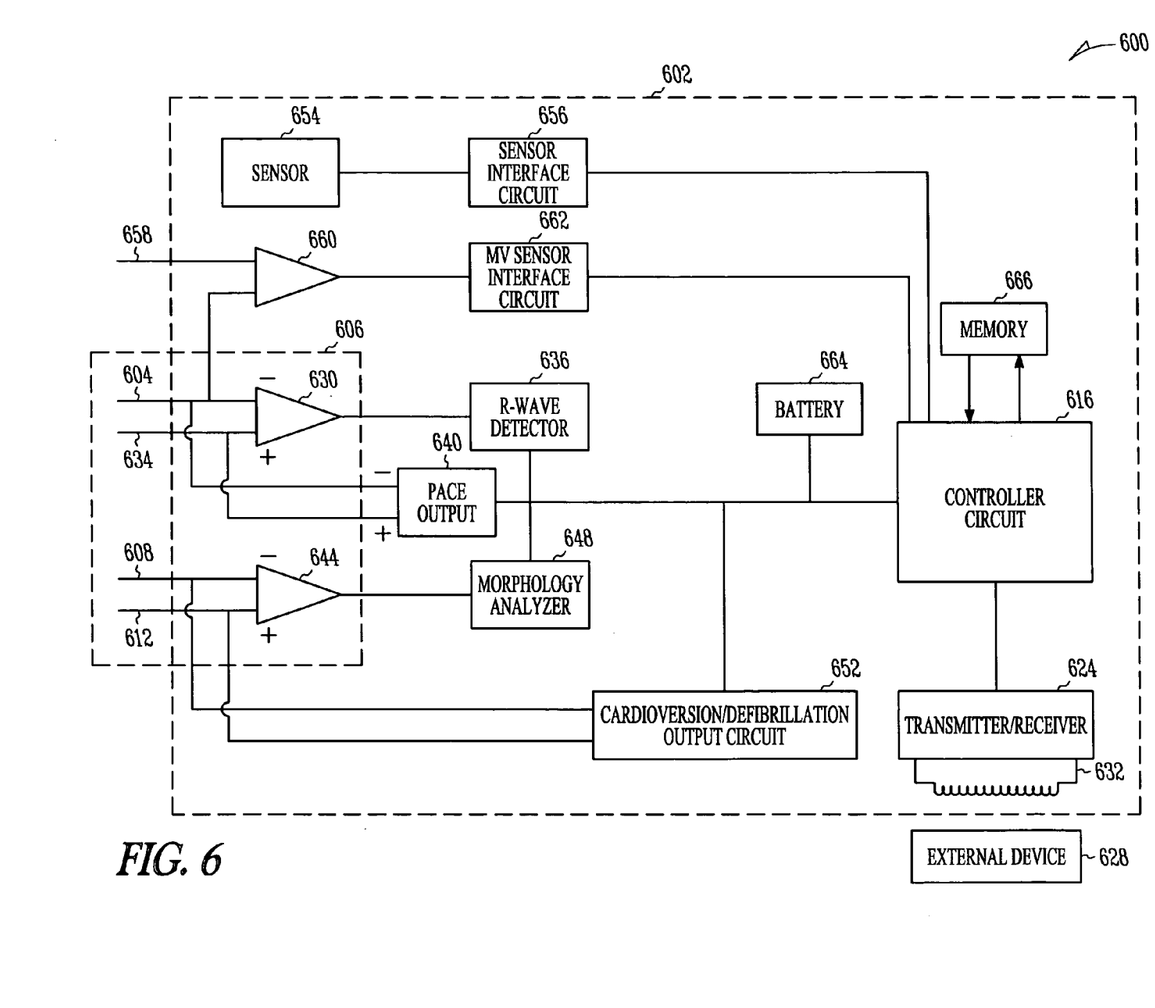
FIG. 6 is an illustration of portions of another embodiment of an implantable medical device used to detect ventricular ectopy in relation to exercise.

FIG. 6 is an illustration 600 of portions of another embodiment of an IMD 602 used to detect ventricular ectopy in relation to exercise. The IMD 602 is powered by battery 664 and includes sensing circuits 606. The sensing circuits 606 include electrical terminals 604, 634, 608, 612 coupled to sense amplifiers 630, 644. The electrical terminals 604, 634, 608, 612 are further coupled to electrodes placed in locations about a heart such as a ventricle or atrium. Examples of electrodes include tip and ring electrodes attached to cardiac leads. Electrical terminals 604, 634 are coupled to electrodes in communication with a ventricle. Sense amplifier 630 is coupled to an R-wave detector 636 which is in turn coupled to a controller circuit 616 and a morphology analyzer circuit 648. The morphology analyzer circuit 648 receives and processes the cardiac complexes detected from the heart signals. Memory 666 stores morphology templates representative of ventricular ectopy. The morphology analyzer circuit 648 compares sampled values of the heart signal to features of at least one morphology template to determine if ventricular ectopy occurred.

The controller circuit 616 is operable to detect exercise and/or recovery from exercise using heart rate or using the activity signals provided by sensor 654, sensor interface circuit 656 and the MV sensor interface circuit 662. In one embodiment, the sensor 654 includes an accelerometer. MV sensor interface circuit 662 processes signals provided by sense amplifier 660. The sense amplifier 660 is coupled to electrical terminals 658, 604 and senses voltage signals across a patient's thorax. In one embodiment, electrical terminal 658 is connected in an insulating header of the IMD or is connected to a can enclosing the IMD. Electrical terminal 604 is positioned at the heart across the patient's thorax from the can or header. The controller circuit 616 is operable to determine whether ventricular ectopy occurred during exercise and/or recovery from exercise from the outputs of the morphology analyzer circuit 648 and the sensor interface circuits 656, 662.

The IMD 602 includes therapy circuits in the form of a pacing output circuit 640 and a cardioversion/defibrillation output circuit 652. In one embodiment, the controller circuit 616 is operable to modify an output of the therapy circuit if ventricular ectopy in the form of tachyarrhythmia occurs during at least one of exercise and recovery from exercise. For example, if the controller circuit 616 detects tachyarrhythmia, the controller circuit 616 is operable to modify parameters of the pacing output circuit 640 to deliver anti-tachyarrhythmia pacing (ATP) or to initiate defibrillation shock therapy using the cardioversion/defibrillation output circuit 652.

Memory 666 is also used to store information related to ventricular ectopy events that occur during at least one of exercise and recovery from exercise. Transmitter/receiver circuit 624 and antenna 632 are used to communicate with external device 628 using wireless communication signals. The information related to ventricular ectopy stored in the memory 666 can be transmitted to external device 628, or the information can be transmitted immediately to the external device as it is gathered.

Figure 7:
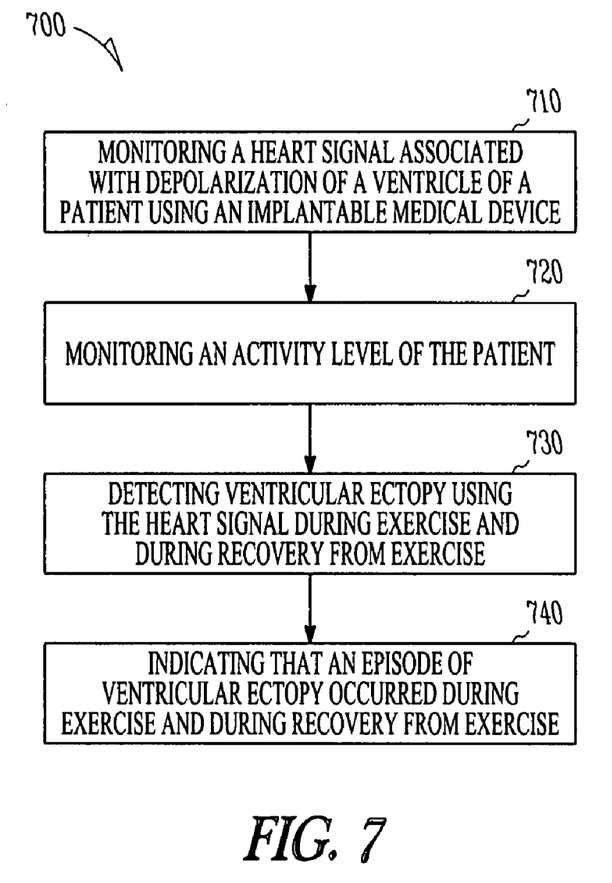
FIG. 7 shows a block diagram of an embodiment of a method for detecting ventricular ectopy in relation to exercise.

FIG. 7 shows a block diagram 700 of a method for detecting ventricular ectopy in relation to exercise. At 710, a heart signal including ventricular depolarizations of a patient is monitored using an IMD. The IMD includes a pacer, a defibrillator, a cardiac resynchronization therapy (CRT) device, or a combination of such devices. It also includes devices that provide a drug therapy in response to sensed heart signals. It further includes IMDs that are purely diagnostic in nature and do not provide a therapy in response to the sensed heart signal or signals.

At 720, an activity level of the patient is monitored to detect exercise and recovery from exercise. The activity level can be monitored through a change in heart rate or using a sensor or sensors. Such sensors include an accelerometer or an MV sensor. At 730, it is determined whether ventricular ectopy occurs during the recovery from exercise using the heart signal. At 740, at least one warning is provided if at least one instance of ventricular ectopy occurs during the recovery from exercise. In one embodiment, the warning is from the IMD itself, such as by an audio alarm. In another embodiment, the warning is transmitted to an external device which gives the alarm. The external device may be a device for use by a patient or a care giver and the alarm may be an audio alarm, a visual display or a combination to draw a care giver's or patient's attention to the condition. The external device may be an IMD programmer or only a monitoring device. In another embodiment, the external device is able to communicate using a communication network such as the internet, a hospital local area network, or a communication network. In such an embodiment, the external device is operable to communicate the warning over the communication network.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method comprising:
    monitoring a heart signal including ventricular depolarizations of a patient using an implantable medical device;
    monitoring an activity level of the patient to detect exercise;
    determining whether ventricular ectopy occurs during the exercise using a comparison of the heart signal to at least one morphology template representative of ventricular ectopy; and
    providing at least one warning if at least one instance of ventricular ectopy occurs during the exercise.

2. The method of claim 1, wherein providing a warning includes communicating at least one warning from the implantable medical device to an external device.

3. The method of claim 1, wherein providing at least one warning includes communicating information related to ventricular ectopy during exercise to an external device.

4. A method comprising:
    monitoring a heart signal including ventricular depolarizations of a patient using an implantable medical device;
    monitoring an activity level of the patient to detect exercise and recovery from exercise;
    determining whether ventricular ectopy occurs during the recovery from exercise using a comparison of the heart signal to at least one morphology template representative of ventricular ectopy; and
    providing at least one warning if at least one instance of ventricular ectopy occurs during the recovery from exercise.

5. The method of claim 4, wherein providing a warning includes providing the warning when a number of instances of ventricular ectopy exceeds a numeric threshold.

6. The method of claim 4, wherein determining whether ventricular ectopy occurs includes:
    comparing a morphology of the heart signal to a morphology of a predetermined cardiac condition of ventricular ectopy; and
    determining whether a ventricular ectopy event occurs using the comparison.

7. The method of claim 4, wherein determining whether ventricular ectopy includes:
    detecting ventricular depolarizations using the heart signal;
    measuring intervals between ventricular depolarizations; and
    determining whether a ventricular ectopy event occurs using the measured intervals.

8. The method of claim 4, wherein monitoring an activity level of the patient includes monitoring a minute ventilation (MV) of the patient using the implantable medical device.

9. The method of claim 4, wherein monitoring an activity level of the patient includes monitoring acceleration using the implantable medical device.

10. The method of claim 4, wherein providing a warning includes communicating a warning from the implantable medical device to an external device.

11. The method of claim 4, wherein providing a warning includes communicating information related to ventricular ectopy during at least one of exercise and recovery from exercise to an external device.

12. The method of claim 4, wherein the method further includes:
   determining whether ventricular ectopy occurs during the exercise using the heart signal; and
   providing at least one warning if at least one instance of ventricular ectopy occurred during the exercise.

13. The method of claim 12, wherein the method further includes providing at least one warning if ventricular ectopy occurs during both exercise and recovery from exercise.

14. A system comprising:
   an implantable medical device (IMD) comprising:
      a ventricular heart signal sensing circuit to provide a ventricular heart signal;
      at least one sensor operable to provide an electrical signal representative of patient activity;
      a sensor interface circuit coupled to the at least one sensor to provide an activity signal; and
      a controller circuit coupled to the heart signal sensing circuit and the sensor interface circuit, wherein the controller is operable to:
         determine whether ventricular ectopy occurs during exercise using a comparison of the heart signal to at least one morphology template representative of ventricular ectopy; and
         provide at least one warning indication if ventricular ectopy occurs during the exercise.

15. The system of claim 14, wherein the system further includes an external device operable to communicate with the implantable device, wherein the external device includes a display, and wherein the external device is operable to display information related to ventricular ectopy occurring during exercise.

16. The system of claim 15, wherein the information related to ventricular ectopy includes at least one warning that ventricular ectopy occurred during exercise.

17. A system comprising:
   an implantable medical device (IMD) comprising:
      a ventricular heart signal sensing circuit to provide a ventricular heart signal;
      at least one sensor operable to provide an electrical signal representative of patient activity;
      a sensor interface circuit coupled to the at least one sensor to provide an activity signal; and
      a controller circuit coupled to the heart signal sensing circuit and the sensor interface circuit, wherein the controller circuit is operable to:
         determine whether ventricular ectopy occurs during recovery from exercise using a comparison of the heart signal to at least one morphology template representative of ventricular ectopy; and
         set at least one warning indicator if ventricular ectopy occurs during the recovery from exercise.

18. The system of claim 17, wherein the implantable medical device further includes:
   a memory coupled to the controller circuit, the memory to store at least one morphology template representative of ventricular ectopy;
   a sampling circuit coupled to the sensing circuit and the controller circuit, the sampling circuit to provide sampled values of the ventricular heart signal; and
   wherein the controller circuit is farther operable to determine whether ventricular ectopy occurs using a comparison of the sampled values to the at least one morphology template representative of ventricular ectopy.

19. The system of claim 17, wherein the sensor includes a minute ventilation (MV) sensor.

20. The system of claim 17, wherein the sensor includes an accelerometer.

21. The system of claim 17, wherein the at least one sensor includes both an MV sensor and an accelerometer sensor.

22. The system of claim 17, wherein the controller circuit is further operable to:
   determine whether ventricular ectopy occurs during exercise using the heart signal; and
   set at least one warning indicator if ventricular ectopy occurs during the exercise.

23. The system of claim 22, wherein the implantable medical device further includes a therapy circuit to provide a therapy to patient, the therapy circuit coupled to the controller circuit, and wherein the controller circuit is further operable to modify an output of the therapy circuit if ventricular ectopy occurs during at least one of exercise and recovery from exercise.

24. The system of claim 22, wherein the controller circuit is further operable to set at least one warning indicator if ventricular ectopy occurs during exercise and during recovery from exercise.

25. The system of claim 24, wherein the system further includes an external device operable to communicate with the implantable device, wherein the external device includes a display, and wherein the external device is operable to display information related to ventricular ectopy occurring during at least one of exercise and recovery from exercise.

26. The system of claim 25, wherein the implantable medical device includes a memory coupled to the controller circuit, the controller circuit operable to store in the memory information related to ventricular ectopy events that occur during at least one of exercise and recovery from exercise.

27. The system of claim 25, wherein the information related to ventricular ectopy includes a histogram of ventricular ectopy during at least one of exercise and recovery from exercise.

28. The system of claim 25, wherein the information related to ventricular ectopy includes trending of ventricular ectopy during at least one of exercise and recovery from exercise.

29. The system of claim 25, wherein the external device is operable to communicate with a communication network.

30. The system of claim 25, wherein the information related to ventricular ectopy includes a warning indicator if ventricular ectopy occurred during at least one of exercise and recovery from exercise, and wherein the warning is indicated when the implantable medical device is interrogated by the external device.

31. The system of claim 30, wherein the external device is operable by a patient, and wherein the warning indicator includes an alarm.

* * * * *

UNITED STATES PATENT AND TRADEMARK OFFICE
CERTIFICATE OF CORRECTION

PATENT NO. : 7,277,756 B2  Page 1 of 1
APPLICATION NO. : 10/919075
DATED : October 2, 2007
INVENTOR(S) : Smith et al.

It is certified that error appears in the above-identified patent and that said Letters Patent is hereby corrected as shown below:

On the Title Page, Item -56-
In field (56), under "Other Publications", line 4, delete "1508," and insert -- 1508), --, therefor.

On the Title Page, Item in "Primary Examiner", line 1, delete "Droesh" and insert -- Droesch --, therefor.

In column 9, line 61, in Claim 18, delete "farther" and insert -- further --, therefor.

Signed and Sealed this

Twenty Second Day of April, 2008

JON W. DUDAS
*Director of the United States Patent and Trademark Office*